United States Patent [19]

Suzuki

[11] 4,207,074
[45] Jun. 10, 1980

[54] LIQUID SAMPLE DISTRIBUTOR

[75] Inventor: Nobuyoshi Suzuki, Hachioji, Japan

[73] Assignee: Olympus Optical Company Ltd., Japan

[21] Appl. No.: 879,131

[22] Filed: Feb. 21, 1978

[30] Foreign Application Priority Data

Feb. 25, 1977 [JP] Japan .................. 52-22089[U]

[51] Int. Cl.² ........................ G01N 1/14; G01N 33/00
[52] U.S. Cl. .................. 23/230 R; 73/425.6; 422/63; 422/81
[58] Field of Search ........ 23/259, 230 R, 253 R (U.S. only); 73/423 A, 425.6; 422/63, 81; 141/130

[56] References Cited

U.S. PATENT DOCUMENTS

| | | | |
|---|---|---|---|
| 3,484,207 | 12/1969 | Anthon | 23/259 X |
| 3,666,420 | 5/1972 | Paatzsch | 23/253 R |
| 3,848,470 | 11/1974 | Hargash et al. | 23/259 X |
| 3,948,605 | 4/1976 | Atwood et al. | 23/259 |
| 3,948,607 | 4/1976 | Atwood et al. | 23/259 |
| 3,963,148 | 6/1976 | Proni et al. | 23/259 X |

*Primary Examiner*—Joseph Scovronek

*Attorney, Agent, or Firm*—Lerner, David, Littenberg & Samuel

[57] ABSTRACT

A liquid sample distributor comprises a sample transfer tube having a nozzle at one end for suction and discharge of a sample, a first switchable valve located intermediate the length of the sample transfer tube, a first sample suction pump and a second sample discharge pump located on the opposite sides of the first switchable valve and connected with the sample transfer tube, a second switchable valve connected with the other end of the transfer tube, and a rinsing water vessel connected with the transfer tube through the second switchable valve. The displacement of the second pump is equal to the quantity of a liquid sample to be distributed while the displacement of the first pump is greater than the given quantity of the liquid sample. A liquid sample is initially suctioned into the nozzle by the first pump in a quantity which is greater than the given quantity to be distributed, and the given quantity thereof is discharged through the second pump for purposes of distribution. Subsequently, the remaining quantity of the liquid sample is discharged by the first pump so as to be discarded. In this manner, a variation in the quantity and the concentration of the liquid sample being distributed is avoided, assuring a smooth distributing operation.

5 Claims, 10 Drawing Figures

LIQUID SAMPLE DISTRIBUTOR

BACKGROUND OF THE INVENTION

The invention relates to a liquid sample distributor which may be used in the distribution of a sample or the like in an automatic analyzer.

In the conventional practice, a sample is distributed into a reaction cell of an automatic analyzer by such techniques as by withdrawing a given quantity of sample into a sample nozzle and flushing it with a diluting liquid, or by withdrawing the given quantity of sample into the sample nozzle and expelling it for distribution by utilizing an air layer. With the former technique, the sample may be diluted or the diluting liquid may find its way into the reaction cell, both of which disadvantageously prevents the achievement of a desired dilution. On the other hand, the latter technique may disadvantageously cause scattering of the sample as a result of an air flow or may prevent a smooth flow of the sample, thus resulting in a loss of the sample.

SUMMARY OF THE INVENTION

It is an object of the invention to provide a liquid sample distributor which completely eliminates the described difficulties by utilizing a pair of pumps.

In accordance with the invention, a liquid sample distributor comprises a sample transfer tube having a nozzle at one end thereof for suction or discharge of a sample, a first switchable valve located intermediate the length of the sample transfer tube, a first sample suction pump and a second sample discharge pump located on opposite sides of the first switchable valve and connected with the sample transfer tube, a second switchable valve connected with the other end of the transfer tube, and a rinsing water vessel connected with the transfer tube through the second switchable valve. The displacement of the second pump is chosen to be equal to a given quantity of liquid sample to be distributed while the displacement of the first pump is chosen greater than the given quantity to be distributed. With the apparatus of the invention, a quantity of liquid sample which is in excess of the given quantity to be distributed is withdrawn into the nozzle by means of the first pump, and the given quantity thereof is then discharged for distribution by means of the second pump. Subsequently, the remaining quantity of liquid sample is entirely discharged by the first pump to be discarded. Subsequently, the remaining quantity of liquid sample is entirely discharged by the first pump and is discarded, thus preventing a variation in the quantity and the concentration of a liquid sample to be distributed in order to assure a smooth distributing operation.

DESCRIPTION OF PREFERRED EMBODIMENTS

Figure 1:
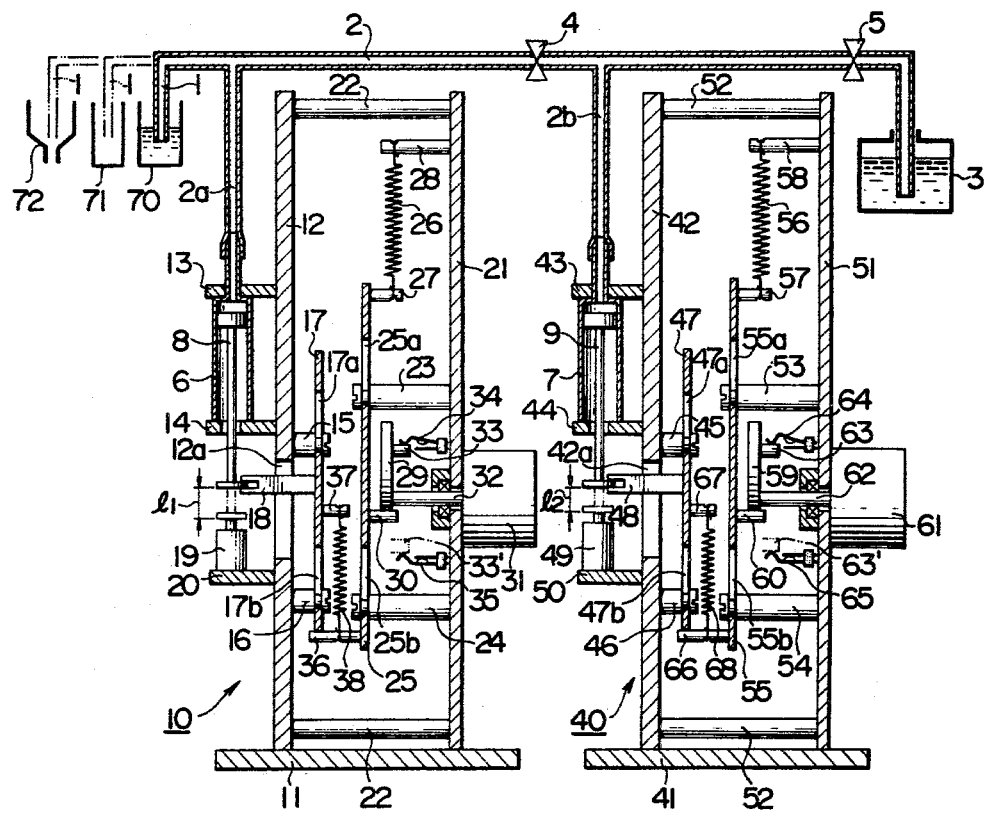
FIG. 1 is an elevational view of a schematic cross section of the liquid sample distributor according to one embodiment of the invention.

Referring to FIG. 1, there is shown a sample transfer tube 2 having a nozzle 1 at one end, which nozzle may be utilized to withdraw or discharge a sample liquid and having its other end connected with a rinsing water vessel 3. A pair of first and second switchable valves 4, 5 are connected along the run of the transfer tube. A first sample suction pump 6 is connected with a portion of transfer tube 2 located between the nozzle 1 and the valve 4 through a branch pipe 2a, and can be operated by a first pump actuator to be described later. Similarly, a second sample discharge pump 7 is connected with a portion of the transfer tube 2 located between the valves 4 and 5 through another branch pipe 2b, and may be operated by a second pump actuator to be described later.

A first pump actuator 10 includes a baseplate 11 on which an upstanding support plate 12 is fixedly mounted for carrying the first pump 6 thereon. The first pump 6 is fixedly mounted between a pair of upper and lower support arms 13, 14, both of which are secured to the outer surface of the support plate 12. A pair of vertically spaced guide pins 15, 16 are secured to the inner surface of the support plate 12 for engagement with a pair of vertically spaced longitudinal guide slots 17a, 17b formed in a movable plate 17, thus supporting the plate 17 in a vertically movable manner. A piston connecting plate 18 extends through a longitudinal guide slot 12a formed in the support plate 12 and has its inner end secured to the movable plate 17. The free end of the piston connecting plate 18 is engaged with the outer end of a piston 8 of the first pump 6. As a consequence, as the movable plate 17 moves in the vertical direction, the piston 8 undergoes a corresponding vertical movement. A stroke pin 19 is mounted on a ledge 20 secured to the outer wall of the support plate 12 at a position below the outer end of the piston 8 for constraining the lower limit of travel of the piston 8. In the embodiment shown, the axial length through which the piston 8 can be moved is chosen equal to a distance $l_1$. Another support plate 21 is fixedly mounted on the baseplate 11 in parallel relationship with the support plate 12, by using at least four ribs or spaces 22. A pair of vertically spaced guide pins 23, 24 are secured on the inner surface wall of the support plate 21 for engagement with a pair of vertically spaced longitudinal guide slots 25a, 25b formed in a slider 25, thus supporting it in a vertically slidable manner. A spring 26 has one end anchored to a pin 27 which is secured to the top end of the slider 25 and its other end anchored to a pin 28 which is secured adjacent to the uppermost end of the inner surface of the support plate 21, and normally urges the slider 25 to move vertically upward. A circular eccentric cam 29 normally bears against a pin 30 from above, which pin is secured to the slider 25 in the central region thereof. The cam is adapted to be driven for rotation by a motor 31, mounted on the outer surface of the support plate 21, through a shaft 32, thereby moving the slider 25 downward. In this manner, the drive from the motor and the spring 26 causes a vertical sliding movement of the slider 25. A switch actuator pin 33 is secured to the cam 29 at a position which is diametrically opposite to the shaft 32, and is effective to operate a pair of motor pause switches 34, 35 at its upper and lower dead center positions, thus causing a temporary pause of the motor rotation. A pin 36 is secured to the lower end of the slider 25, and has its free end disposed in abutment against the lower end of the movable plate 17 as a result of a spring 38 extending between the pin 36 and another pin 37 which is secured to the movable plate 17 in its central region. Thus, it will be understood that the movable plate 17 will be driven upward as the slider 25 slides upward, and will be also driven downward until its movement is interrupted by abutment of piston 8 against the pin 19.

A second pump actuator 40 is constructed essentially in the similar manner as the first pump actuator, and therefore only the designation of its parts will be given without describing the arrangement and operation. Specifically, the second actuator includes a baseplate 41, support plate 42, longitudinal guide slot 42a, upper and lower support arms 43, 44, guide pins 45, 46, movable plate 47, longitudinal guide slots 47a, 47b, piston connecting plate 48, stroke pin 49, ledge 50, support plate 51, ribs or spaces 52, guide pins 53, 54, slider 55, longitudinal guide slots 55a, 55b, spring 56, pins 57, 58, circular eccentric cam 59, pin 60, motor 61, shaft 62, switch actuator pin 63, motor pause switches 64, 65, pins 66, 67 and spring 68. However, it is to be understood that the stroke pin 49 has an axial length which is greater than that of the stroke pin 19 used in the first pump actuator 10, so that the piston 9 of the second pump 7 is only movable within an extent of a length $l_2$ which is less than the stroke or distance $l_1$ of the piston 8 of the first pump 6. If we assume that the displacement of the second pump 7 is chosen equal to a given quantity of liquid sample to be distributed, the displacement of the first pump 6 is greater than this given quantity.

Figure 2:
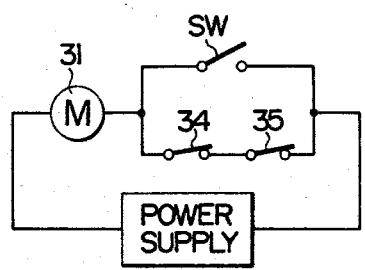
FIG. 2 is a wiring diagram showing one example of a control circuit for a pump drive motor.

The motor pause switches 34, 35 and 64, 65 are connected in circuit relationship with the motors 31, 61 and start switch SW as illustrated in FIG. 2. FIG. 2 shows a typical control circuit for the motor 31, and the circuit comprises motor 31 connected in series with a power supply source and a parallel combination of a normally open start switch SW and a series circuit of the pair of normally closed motor pause switches 34, 35. When the switch actuator pin 33 is located at its upper dead center position, the pause switch 34 is opened to stop the motor 31. If the start switch SW is now closed, the motor 31 can be set in motion. Subsequently, the rotation of the motor 31 causes a corresponding rotation of the cam 29 and the pin 33 moves through a region where neither pause switch 34 nor 35 is depressed, whereby the motor 31 continues to rotate if the start switch SW is opened. When the pin 33 reaches its lower dead center during the rotation of the motor 31, the pause switch 35 is opened to deenergize the motor. Subsequently when the start switch SW is closed again, the motor 31 is set in motion again and continues to rotate until the pin 33 opens the switch 34. In this manner, the liquid sample suction and discharge operations take place under control of the pump 6. Obviously, the pump 7 operates in a similar fashion.

The operation of the distributor of the invention will now be described with reference to FIGS. 3 to 11. It should be understood that in these Figures, a thick line represents the transfer of rinsing water while dotted lines represent the transfer of a liquid sample within the transfer tube 2.

Figure 3:
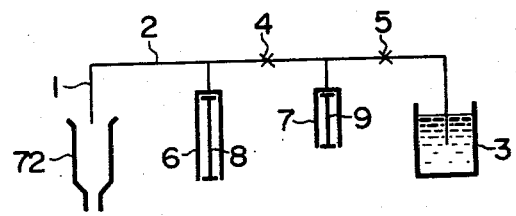
FIGS. 3 and 10 are schematic views illustrating a sequence of operations performed by the apparatus of the invention.

FIG. 3 shows an initial condition when the transfer tube 2 is empty of liquid, the valves 4, 5 are both closed and the pistons 8, 9 of the pumps 6, 7 are located at their upper dead center. At this time, a drain vessel 72 is brought to a position below the nozzle 1. Under this condition, the valve 5 may be opened while maintaining the valve 4 closed, and the start switch for the motor 61 can be turned on to actuate the second pump actuator 40 when the piston 9 of the second pump 7 is at its upper dead center. Thereupon, the motor 61 begins and continues to rotate until the pin 63 reaches position 63' (see FIG. 1) i.e. its lower dead center position to operate the pause switch 65. When the motor is temporarily stopped, the piston 9 moves down through the distance $l_2$ until it bears against the stop or stroke pin 49, whereupon it remains stationary for a time. In the meantime, a quantity of rinsing water is withdrawn into the transfer tube 2 from the vessel 3, as indicated in FIG. 4.

Figure 4:
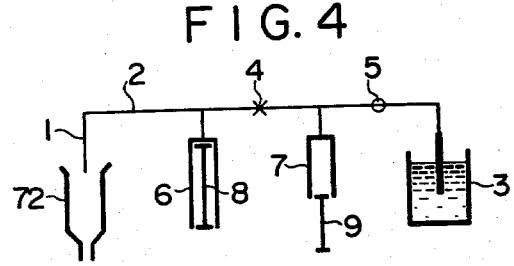
Figure 5:
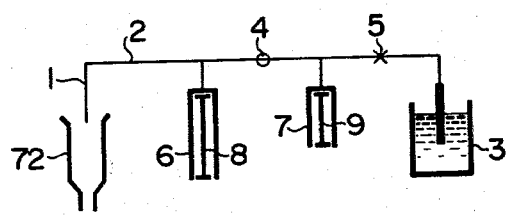

Under the condition shown in FIG. 4, the valve 4 is then opened while the valve 5 is closed, and the start switch for the motor 61 is turned on again to operate the second pump actuator 40. Then the motor 61 begins and continues to rotate until the pin 63 reaches the upper dead center position to operate the pause switch 64, whereupon it temporarily stops the piston 9 at its upper dead center position. In the meantime, the air present within the transfer tube 2 is exhausted by an amount corresponding to the displacement of the second pump 7 (see FIG. 5).

By repeating the opening and closing of the valves 4, 5 and the operation of the second pump 7, the entire transfer tube 2 including the nozzle 1 can be filled with rinsing water. The filling of the transfer tube with the rinsing water can be achieved by simultaneously operating the first pump 6 together with the second pump 2 as the valves 4, 5 are opened and closed in a suitable manner.

Figure 6:
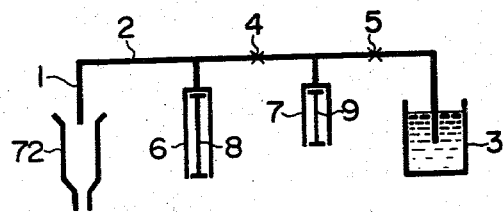
Figure 7:
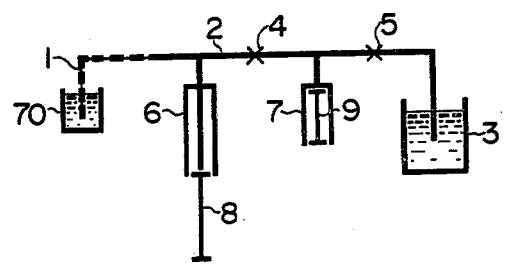

When the apparatus assumes the condition shown in FIG. 6, valves 4, 5 are both closed and the sample nozzle 1 is brought into a sample cup 70. Then, the start switch SW for the motor 31 is turned on to operate the first pump actuator 10. The motor 31 then begins and continues to rotate until the pin 33 reaches position 33', i.e. its lower dead center position to operate the pause switch 35, whereupon the motor 31 comes to a stop. The piston 8 has moved down through the distance $l_1$ until it bears against the stop pin 19, and then remains stationary. In the meantime, a quantity of liquid sample which is in excess of the given quantity to be distributed will be withdrawn into the nozzle 1 from the cup 70, as shown in FIG. 7.

Figure 8:
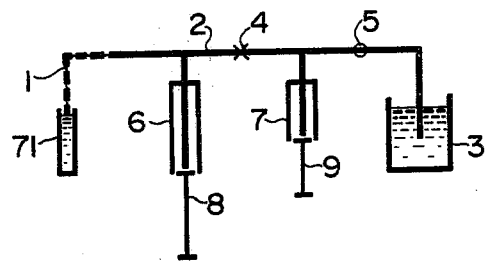

Subsequently, the valve 4 is closed while the valve 5 is opened, and the sample nozzle 1 is moved over a reaction cell 71. By turning on the start switch for the motor 61, the second pump actuator 40 is operated. Then the motor 61 begins and continues to rotate until the pin 63 reaches its lower dead center position to open the pause switch 65, whereupon motor G1 and pin 63 come to a stop. The piston 9 has moved down through the distance $l_2$ until it bears against the stop pin 49, and then remains stationary. In the meantime, an additional amount of rinsing water which is equal to the given quantity of liquid sample to be distributed will be withdrawn into the transfer tube 2 from the vessel 3, as shown in FIG. 8.

Figure 9:
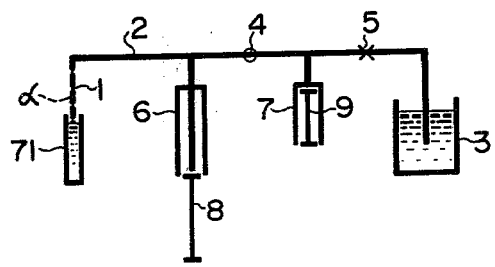
Figure 10:
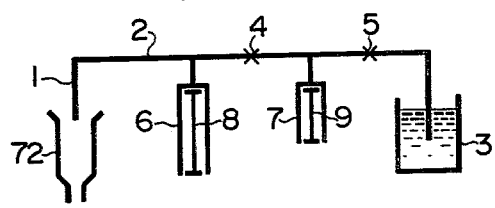

The valve 4 is now opened while the valve 5 is closed, and the start switch for the motor 61 is turned on again to operate the second pump actuator 40. This causes the motor 61 to rotate until the pin 63 reaches its upper dead center position to operate the pause switch 64, where it comes to a stop. The piston 9 has moved upward until the upper dead center is reached, and then remains stationary. In the meantime, the given quantity of liquid sample is injected from the nozzle 1 into the reaction cell 71, as shown in FIG. 9.

Both valves 4, 5 are then closed, and the nozzle 1 is moved to a position over the drain vessel 72, and the start switch SW for the motor 31 is turned on to operate the first actuator 10. This causes the motor 31 to rotate until the pin 33 reaches its upper dead center to operate the pause switch 34, whereupon it comes to a stop. The piston 8 has moved upward until the upper dead center position is reached, and then remains stationary. In the meantime, any excess amount of liquid sample which remained in the nozzle 1 as well as the given quantity of rinsing water contained within the transfer tube 2 are discharged through the nozzle 1 into the drain vessel 72, and simultaneously achieves a washing action of the nozzle 1 (see FIG. 10). This completes one cycle of sample liquid distributing operation. Additional cycles of distributing operations can be conducted to supply the liquid sample into other reaction cells, by returning from the step of FIG. 10 to FIG. 7 and repeating the steps shown in FIGS. 7 to 10.

As described above, the liquid distributor according to the invention withdraws a sample liquid in an amount which exceeds the given quantity and then injects the latter. This avoids the dilution of the injected sample quantity by the rinsing water or diluting liquid, and also avoids the loss of the sample. The quantity of sample liquid to be distributed can be freely adjusted by a suitable choice of the length of the pin.

It is to be noted that the liquid quantity withdrawn or discharged by the first pump 6 is almost entirely contained in that region of the transfer tube 2 which is associated with the nozzle 1, thus preventing the liquid sample from flowing into the pump 6 to give rise to the possibility of dilution.

What is claimed is:

1. A method for withdrawing and dispensing a sample liquid from a tube filled with a rinsing liquid, said tube having first and second open ends, first and second tube branches respectively spaced inwardly from said first and second tube ends, a first valve connected between said first and second branches, a second valve connected between said second branch and said second end, a first pump in said first branch between said first open end and said first valve, and a second pump in said second branch between said second open end and said second valve, the method comprising the steps of:
   (a) inserting said first open end of said tube into a sample liquid container;
   (b) closing said first and second valve and drawing a first predetermined quantity of rinsing liquid into said first pump from said first branch to cause a corresponding predetermined quantity of sample liquid to be drawn into said first branch through said first open end of said tube;
   (c) opening said second valve and drawing a second predetermined quantity of rinsing liquid into said second pump through said second branch and said second open end of said tube, said second predetermined quantity of rinsing liquid being less than said first predetermined quantity of rinsing liquid; and
   (d) closing said second valve, opening said first valve and pumping said second predetermined quantity of rinsing liquid back into said second branch of said tube, to urge a corresponding predetermined portion of said predetermined quantity of said sample liquid to exit through said first open end of said tube.

2. A method according to claim 1, wherein said corresponding predetermined portion of said predetermined quantity of said liquid sample is urged out of said first open end of said tube in one continuous operation.

3. An apparatus for distributing a liquid sample, comprising a source of liquid sample, a source of rinsing liquid, a tube having a first opening at one end thereof and a second opening at the other end thereof, first valve means located along said tube intermediate said one end and said other end thereof for regulating the liquid flow through said tube, first pump means located along said tube between said one end thereof and said first valve means for drawing a predetermined amount of liquid sample from said source of liquid sample into said tube through said first opening, said first pump means having a displacement equal to said predetermined amount of liquid sample, second valve means located along said tube between said other end thereof and said first valve means for regulating the liquid flow through said tube, and second pump means located along said tube between said first valve means and said second valve means for drawing a predetermined amount of rinsing liquid from said source of rinsing liquid into said tube through said second opening and for dispensing a predetermined portion of said predetermined amount of liquid sample from said tube through said first opening by using said predetermined amount of rinsing liquid to displace and dispense said predetermined portion of said predetermined amount of liquid sample, said predetermined portion of said predetermined amount of liquid sample being equal to said predetermined amount of rinsing liquid and said second pump means having a displacement equal to said predetermined portion of said predetermined amount of liquid sample and less than the displacement of said first pump means.

4. An apparatus according to claim 3, wherein said displacement of said first pump means is adjustable.

5. An apparatus according to claim 3, wherein said displacement of said second pump means is adjustable.

* * * * *

UNITED STATES PATENT AND TRADEMARK OFFICE
CERTIFICATE OF CORRECTION

PATENT NO. : 4,207,074
DATED : June 10, 1980
INVENTOR(S) : Nobuyoshi Suzuki

It is certified that error appears in the above-identified patent and that said Letters Patent are hereby corrected as shown below:

Column 2, line 40; and column 3, line 15; change "spaces" to --spacers--.

Column 2, line 42, delete "wall".

Claim 1, column 5, line 46, change "valve" to --valves--.

Claim 1, column 6, line 8, delete the comma.

Signed and Sealed this

Seventh Day of April 1981

[SEAL]

Attest:

RENE D. TEGTMEYER

Attesting Officer

Acting Commissioner of Patents and Trademarks